Feb. 19, 1974 G. BANDONI Plant Pat. 3,490
ALMOND TREE
Filed Oct. 2, 1972
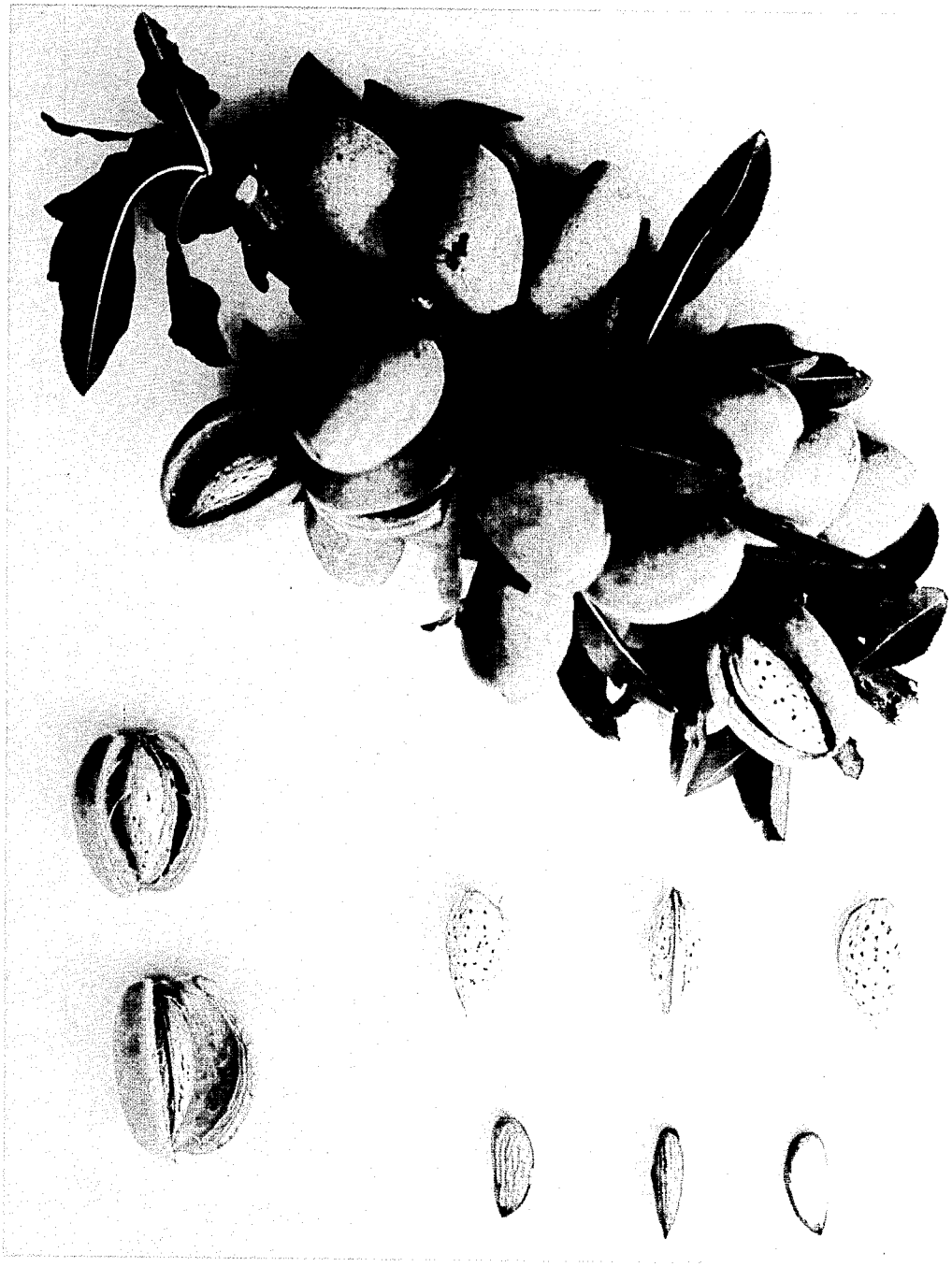

United States Patent Office

Plant Pat. 3,490

Patented Feb. 19, 1974

3,490

ALMOND TREE

Guido Bandoni, 1434 N. Franklin Road,
Merced, Calif. 95390

Filed Oct. 2, 1972, Ser. No. 294,029
Int. Cl. A01h 5/03
U.S. Cl. Plt.—30 1 Claim

ABSTRACT OF THE DISCLOSURE

A large, dense, vigorous almond tree—which produces at an early age—having a stocky trunk with strong branches, abundant foliage, and a very heavy, early, white bloom; the tree being a regular and very productive bearer of large, uniform, very light colored nuts in harvest in late September, and having large, single, plump kernels.

BACKGROUND OF THE VARIETY

In the trade improved varieties of almond trees are being sought for commercial growing, and to this end I have conducted an experimental development program seeking new and distinct varieties of commercially acceptable almond trees. The present variety of almond tree was originated by me in the course of such endeavor.

ORIGIN OF THE VARIETY

The present variety of almond tree was originated by me in my orchard located in Merced County, California, in the following manner:

Seeds gathered from a bitter nut tree (unpatented) in such orchard were planted, and the seedlings therefrom grown in an experimental plot. Of such resultant seedlings, and which were open-pollinated, one—and which is the present variety—evidenced, upon bearing a crop, certain desirable characteristics (both in tree and nuts) for commercial growing, and such one seedling was, therefore, selected by me for asexual reproduction.

ASEXUAL REPRODUCTION OF THE VARIETY

Subsequent to origination of the present variety of almond tree in the manner above described, I asexually reproduced such variety by grafting it on other trees in my orchard located as aforesaid, and—in maturity—such asexual reproductions ran true to the original tree in all respects.

SUMMARY OF THE VARIETY

The present variety of almond tree is, characteristically, of large size, dense, vigorous in growth, bears a crop at a very early age, has a stocky trunk with strong branches, abundant foliage, and a very heavy, early, white bloom which is only a few days after the Ne Plus Ultra (unpatented); the tree being a regular and very productive bearer of large, uniform, very light colored nuts in harvest in late September about with said Ne Plus Ultra; and the kernels being large, single, and plump. The very light color of the nuts gives the appearance of nuts which have been blanched.

The present variety of almond tree is additionally characterized by a white bloom which is short, like the Jordanolo (unpatented), and just as resistant to damage by freezing.

The present variety of almond tree is further characterized by general resemblance to the Ne Plus Ultra in foliage and nut size, but the tree is more upright in growing habit, and the wood is stronger.

The present variety of almond tree is still further characterized by the retention of its short spurs on the branches from the base to adjacent the tips; this assuring, desirably, of a good distribution of the nuts on the tree. As the nuts are well distributed, so is the weight thereof, and which minimizes limb breakage.

The present variety of almond tree is also characterized by being a strong pollinator for the Nonpareil (unpatented) and the Ne Plus Ultra.

BRIEF DESCRIPTION OF THE DRAWING

The drawing is an illustration, by photographic reproduction in color, of a twig with leaves and nuts, detached nuts in hull, nuts out of hull, and meats.

DESCRIPTION OF THE VARIETY

The botanical details of this new and distinct variety of almond tree—with color definitions (except those in common color terms) referenced to Maerz and Paul Dictionary of Color—are as follows:

Tree:
- *Size.*—Large.
- *Density.*—Dense.
- *Vigor.*—Vigorous.

Trunk:
- *Form.*—Stocky.
- *Texture.*—Smooth.

Branches:
- *Form.*—Stocky. Main branches thick at inner ends—tapering to outer ends.
- *Texture.*—Smooth.
- *Lenticels.*—Number, medium. Size, medium.
- *Branching habit.*—Medium.
- *Color.*—New wood—brown. Mature wood—brown.

Foliage:
- *Quantity.*—Abundant.

Leaves:
- *Size.*—Large. Average length—3½" (including petiole). Average width—1".
- *Shape.*—Ovate, acutely pointed.
- *Thickness.*—Medium.
- *Texture.*—Smooth.
- *Margin.*—Crenate.
- *Petiole.*—Length, medium. Thickness, medium.
- *Glands.*—Average number—2. Small, globose. Positioned laterally on petiole.
- *Color.*—Top side—Glossy dark green (23–L–8). Under side—Lighter green (22–L–8).

Bloom:
- *Amount of bloom.*—Very heavy.
- *Color.*—White.
- *Blooming period.*—Early. First blossoms—Feb. 26. Average season—a few days after the Ne Plus Ultra.

Crop:
- *Bearing.*—Regular bearer.
- *Productivity.*—Very heavy.
- *Distribution of nuts on tree.*—Well distributed.
- *Harvest period.*—Medium. Late September—about with Ne Plus Ultra.
- *Tenacity.*—Hangs well on tree. Easy to harvest. Easy to hull.

Hull:
- *Outer surface.*—Smooth.
- *Form.*—Regular.
- *Thickness.*—Thick.
- *Flesh.*—Fleshy.
- *Suture.*—Ridged.
- *Color.*—Before dehiscence—light green (20–I–7) with a silvery sheen, shading—at dehiscence—to a light yellowish-green (20–K–5).
- *Dehiscence.*—Opens freely.
- *Splitting.*—Along suture.

Nut:

*Size.*—Large. Average length—1⅜". Average width —13/16". Average thickness—7/16". Average weight —112 nuts per pound.

*Form.*—Length/width, elongated. Width/thickness, plump.

*Shell.*—Soft. Outer shell: Hard. Inner shell: Soft, well sealed.

*Color.*—Light straw (10–E–4).

*Pit.*—Large, few, deep, irregular.

*Base.*—Square.

*Stem scar.*—Small, obtuse.

*Apex.*—Acute.

*Wing.*—Broad, thin, tapered toward base.

*Inner surface.*—Light.

*Ventral streak.*—Light, narrow, long, point acute.

*Percentage of kernel to nut.*—1971 crop—63.2%.

Kernel:

*Size.*—Large. Average length—13/16". Average width 9/16". Average thickness—5/16".

*Kernels per ounce on average sample.*—18.

*Form.*—Length/width, elongated. Width/thickness, plump.

*Base.*—Ventrally oblique.

*Stem scar.*—Small, obtuse.

*Apex.*—Acute.

*Surface.*—Furrowed.

*Pellicle.*—Thick.

*Pubescence.*—Rough.

*Color.*—Tan (10–D–11).

*Number of doubles.*—None.

*Flavor.*—Dry, sweet.

*Quality.*—Very good.

*Susceptibility or resistance to insects and diseases*: No unusual susceptibilities noted, and apparently excellent resistance to common diseases of almond trees.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is large, dense, vigorous, bears a crop at a very early age, has a stocky trunk with strong branches on which short spurs are retained from the base to adjacent the tips, has abundant foliage, and a very heavy, early, white bloom which is only a few days after the Ne Plus Ultra, the blossoms being short like the Jordanolo, and equally resistant to damage by freezing; the tree being a regular and very productive bearer of large, uniform, very light-colored nuts in harvest in late September about with the Ne Plus Ultra, and the kernels being large, single, and plump; there being general resemblance in foliage and nut size to the Ne Plus Ultra, but the tree of the present variety is more upright in growing habit, and the wood is stronger.

No references cited.

ROBERT E. BAGWILL, Primary Examiner